(12) United States Patent
Choi et al.

(10) Patent No.: US 9,848,841 B2
(45) Date of Patent: Dec. 26, 2017

(54) X-RAY STITCHING JIG

(71) Applicant: SAMSUNG ELECTRONICS CO., LTD., Suwon-si, Gyeonggi-do (KR)

(72) Inventors: Sang Geun Choi, Uiwang-si (KR); Suk Hee Won, Incheon (KR); Hyun Joong Chae, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/339,711

(22) Filed: Jul. 24, 2014

(65) Prior Publication Data

US 2015/0030135 A1  Jan. 29, 2015

(30) Foreign Application Priority Data

Jul. 26, 2013  (KR) .................. 10-2013-0088623

(51) Int. Cl.
  *A61B 6/00* (2006.01)
  *G01N 23/04* (2006.01)
  *A61B 6/04* (2006.01)

(52) U.S. Cl.
  CPC .............. *A61B 6/4429* (2013.01); *A61B 6/04* (2013.01); *A61B 6/4405* (2013.01); *A61B 6/4452* (2013.01); *A61B 6/5235* (2013.01); *A61B 6/5241* (2013.01); *G01N 23/04* (2013.01); *G01N 2223/32* (2013.01)

(58) Field of Classification Search
  CPC ....... A61B 6/04; A61B 6/4405; A61B 6/4452; A61B 6/5235; A61B 6/5241; A61B 6/4429

USPC .............. 378/62, 98.12, 146, 189, 190, 192, 378/196–198
See application file for complete search history.

(56) References Cited

U.S. PATENT DOCUMENTS

| | | | | |
|---|---|---|---|---|
| 5,216,700 A | * | 6/1993 | Cherian | A61B 6/08 378/163 |
| 5,452,721 A | * | 9/1995 | Hacker | A61B 6/08 250/363.02 |
| 5,693,954 A | * | 12/1997 | Jacobs | H04N 1/00002 250/581 |
| 5,970,119 A | * | 10/1999 | Hofmann | G01B 15/00 378/163 |
| 6,078,699 A | * | 6/2000 | Lobregt | A61B 6/481 348/E5.086 |
| 6,084,941 A | * | 7/2000 | Stenstrom | A61B 5/107 378/162 |
| 6,097,833 A | * | 8/2000 | Lobregt | A61B 6/481 348/E5.089 |

(Continued)

*Primary Examiner* — Allen C. Ho
(74) *Attorney, Agent, or Firm* — Staas & Halsey LLP (57) ABSTRACT

A medical imaging jig is provided with a foldable handle and an integral type foldable footstool, so that a patient having difficulty in movement can be easily and safely subject to medical imaging. In particular, the integral type foldable footstool is provided to be rotated on a hinge to be folded, a lead ruler provided on the rear surface of the medical imaging jig is slidably and detachably provided so that the lead ruler may be moved leftward or rightward or detached depending on the demand by a user, a handle provided on the medical imaging jig may be folded to allow positioning of an objected to be imaged, and omnidirectional wheels are provided on the lower end of the medical imaging jig.

27 Claims, 6 Drawing Sheets

(56) References Cited

U.S. PATENT DOCUMENTS

| | | | | |
|---|---|---|---|---|
| 6,152,598 A | * | 11/2000 | Tomisaki | A61B 6/4233 378/188 |
| 6,282,264 B1 | * | 8/2001 | Smith | A61B 6/0457 378/167 |
| 6,356,621 B1 | * | 3/2002 | Furumori | A61B 6/12 378/162 |
| 6,463,121 B1 | * | 10/2002 | Milnes | A61B 6/4482 378/62 |
| 6,678,353 B2 | * | 1/2004 | Graumann | A61B 6/04 378/163 |
| 6,696,691 B2 | * | 2/2004 | Foos | G03B 42/047 250/484.4 |
| 6,704,388 B2 | * | 3/2004 | Op De Beek | A61B 6/583 250/252.1 |
| 6,907,629 B2 | * | 6/2005 | Longton | A61B 6/04 378/209 |
| 6,979,124 B2 | * | 12/2005 | Gerwin | A61B 6/583 378/18 |
| 7,056,019 B1 | * | 6/2006 | Hanson | A61B 6/583 378/18 |
| 7,114,849 B2 | * | 10/2006 | Atzinger | A61B 6/5241 378/206 |
| 7,142,632 B2 | * | 11/2006 | Atzinger | A61B 6/4225 378/196 |
| 7,313,223 B2 | * | 12/2007 | Unfors | A61B 6/08 250/336.1 |
| 7,357,574 B2 | * | 4/2008 | Matsumoto | A61B 6/04 378/189 |
| 7,396,161 B2 | * | 7/2008 | Schmitt | A61B 6/04 378/204 |
| 7,455,455 B2 | * | 11/2008 | Marinelli | A61B 6/04 378/208 |
| 7,482,601 B2 | * | 1/2009 | Lewis | G03F 7/025 250/472.1 |
| 7,499,579 B2 | * | 3/2009 | Squilla | G06T 7/0004 378/168 |
| 7,522,701 B2 | * | 4/2009 | Jensen | A61B 6/481 378/162 |
| 7,634,308 B2 | * | 12/2009 | Ogawa | A61B 6/481 378/196 |
| 7,712,959 B2 | * | 5/2010 | Tanabe | H01J 31/49 250/370.08 |
| 7,742,570 B2 | * | 6/2010 | Yamaguchi | A61B 6/4441 378/62 |
| 7,874,729 B2 | * | 1/2011 | Okuno | A61B 6/4233 378/205 |
| 7,881,434 B2 | * | 2/2011 | Akahori | A61B 6/4233 378/116 |
| 7,953,206 B2 | * | 5/2011 | Oogami | A61B 6/4429 378/98.12 |
| 7,978,811 B2 | * | 7/2011 | Sakai | A61B 6/4441 378/196 |
| 7,986,769 B2 | * | 7/2011 | Kotani | A61B 6/00 378/62 |
| 8,064,572 B2 | * | 11/2011 | Sato | A61B 6/4429 378/206 |
| 8,084,744 B2 | * | 12/2011 | Enomoto | A61B 6/4441 250/370.09 |
| 8,213,572 B2 | * | 7/2012 | Minnigh | A61B 6/06 378/145 |
| 8,275,187 B2 | * | 9/2012 | Oogami | A61B 6/00 378/174 |
| 8,300,764 B2 | * | 10/2012 | Yamaguchi | G06T 7/0042 378/62 |
| 8,344,327 B2 | * | 1/2013 | Yamaguchi | A61B 6/5241 250/363.07 |
| 8,351,568 B2 | * | 1/2013 | Minnigh | A61B 6/4266 378/204 |
| 8,360,639 B2 | * | 1/2013 | Kato | A61B 6/4233 378/197 |
| 8,755,490 B2 | * | 6/2014 | Takamura | A61B 6/00 378/108 |
| 8,767,913 B2 | * | 7/2014 | Okuno | A61B 6/08 378/206 |
| 8,837,671 B2 | * | 9/2014 | Sakai | A61B 6/06 378/62 |
| 8,873,709 B2 | * | 10/2014 | Kimura | A61B 6/4429 378/165 |
| 8,899,832 B2 | * | 12/2014 | Fabrizio | A61B 6/08 378/195 |
| 8,908,832 B2 | * | 12/2014 | Yamashita | A61B 6/06 378/62 |
| 8,977,028 B2 | * | 3/2015 | Moon | A61B 6/461 382/128 |
| 8,989,348 B2 | * | 3/2015 | Cox | G01N 23/04 378/146 |
| 9,016,940 B2 | * | 4/2015 | Fabrizio | A61B 6/02 378/177 |
| 9,078,597 B2 | * | 7/2015 | Patil | A61B 6/107 |
| 9,149,247 B2 | * | 10/2015 | Lee | A61B 6/4452 |
| 9,177,681 B2 | * | 11/2015 | Morris | G21K 1/046 |
| 9,265,467 B2 | * | 2/2016 | Kamiya | A61B 6/5241 |
| 9,351,696 B2 | * | 5/2016 | Graumann | A61B 6/505 |

* cited by examiner

X-RAY STITCHING JIG

CROSS-REFERENCE TO RELATED APPLICATIONS

This application claims the benefit of Korean Patent Application No. 10-2013-0088623, filed on Jul. 26, 2013, in the Korean Intellectual Property Office, the disclosure of which is incorporated herein by reference.

BACKGROUND

1. Field

Embodiments of the present disclosure relate to an X-ray stitching jig capable of building an environment in which an object to be inspected is effectively and safely photographed according to a state of an object to be inspected.

2. Description of the Related Art

X-radiation (X-rays) refers to electromagnetic waves emitted with a strong transmit power by electrons collided with an object at a high speed. An X-ray apparatus using the X-radiation has an inspection part of a human body interposed between an X-ray tube and an X-ray film, and radiates X-rays from the X-ray tube to be penetrated through the inspection part, so that the penetrated X-rays are detected.

The X-ray apparatus may include an X-ray generator, a detector and a server. The X-ray generator is configured to emit X-rays using a high voltage, and output X-Rays to an object to be inspected. The detector detects the X-rays passing through the object, and transmits information on the detected X-rays.

The X-ray stitching jig has the detector provided so as to vertically move. When the object to be inspected is positioned on a front side of the X-ray stitching jig, the detector moves to detect the X-rays penetrating a predetermined portion of the object to be inspected.

SUMMARY

One or more embodiments relate to an X-ray stitching jig that may, in order to possibly allow a patient, who has difficulty moving, to have an easy and safe X-ray imaging, provide a foldable handle and an integral type foldable footstool, and may have a lead ruler slidably and detachably provided at a rear surface thereof such that the lead ruler may be detached if necessary and may allow leftward and rightward movement depending on the demand by a user, and may have wheels provided at a lower end thereof so as to be rotatable in all directions, thereby possibly achieving easy movement thereof.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

In accordance with one or more embodiments, an X-ray stitching jig may include a base, a transparent plate, a detection part and a footstool base. The transparent plate may be mounted on the base. The detection part may be positioned on a rear side of the transparent plate to detect X-rays passing through an object to be inspected. The footstool base may be provided with an integral type footstool and may be rotatably connected to the base by a hinge.

The base may be provided with a fixing rib and the footstool base may be seated on the fixing rib to be fixed.

As the footstool base is seated on the fixing rib, an upper surface of the footstool base may form one plane with an upper surface of the base.

The transparent plate may be provided with a fluoroscopy window and side frames may be provided at both sides of the fluoroscopy window to support the fluoroscopy window.

The side frame may be provided with an interference part that protrudes forward from the side frame.

The footstool base may be rotated on the hinge and interfered with by the interference part.

The footstool base may be provided with an insertion part, and the side frame may be provided with an insertion hole into which the insertion part may be inserted.

As the footstool base rotates on the hinge, the insertion part may be slidably inserted into the insertion hole, so that the footstool base may be folded to be perpendicular to the base.

The side frame may be provided with a handle that is foldable.

The handle may be provided so as to be rotatable on a rotating shaft that passes through a mounting part protruding from the side frame and to pass through the handle.

A lead ruler may be slidably provided at a rear of the transparent plate.

An upper frame may be provided at an upper side of the transparent plate, and a rail may be provided at a lower surface of the upper frame, so that the lead ruler may be slidable leftward and rightward along the rail.

A fixing bracket may be mounted on an upper portion of the lead ruler, and may be mounted on the rail so as to possibly be capable of sliding.

The upper frame may be further provided at the lower surface thereof with a guide rail, and one side of the fixing bracket may be mounted on an upper surface of the guide rail so as to possibly be capable of sliding.

The fixing bracket may be detachably mounted on the rail.

A rail groove may be formed on the base, and a protrusion part guided by the rail groove may be provided on a lower portion of the lead ruler.

A support part may be provided at a portion connecting the base to the transparent plate to support the transparent plate to possibly prevent the transparent plate from being shaken or tilted.

The base may be provided at a lower portion thereof with a wheel that may be rotatable in all directions.

A stopper positioned on a bottom surface may restrict the wheel from rotating.

The detection part may be provided so as to move upward and downward.

In accordance with one or more embodiments a medical imaging jig may include a base, a detection part mounted on the base and configured to detect electromagnetic radiation passing through an object to be inspected, the detection part being provided so as to move upward and downward and a lead ruler slidably provided above the base and in front of the detection part.

The medical imaging jig of claim may also include side frames extending upward from the base and an upper frame provided at an upper end of each of the side frames and connecting the side frames, and a guide rail may be provided at a lower surface of the upper frame, so that the lead ruler may be slidable leftward and rightward along the guide rail.

A rail groove may be formed on the base, and a protrusion part guided by the rail groove may be provided on a lower portion of the lead ruler.

The medical imaging jig may also include a footstool base provided with an integral type footstool and rotatably connected to the base by a hinge.

The base may be provided with a fixing rib and the footstool base may be seated on the fixing rib to be fixed, and when the footstool base is seated on the fixing rib, an upper surface of the footstool base may form one plane with an upper surface of the base.

One side frame may be provided with a handle that is foldable.

The handle may be provided so as to be rotatable on a rotating shaft that passes through the handle and a mounting part protruding from the one side frame.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to one or more embodiments, illustrated in the accompanying drawings, wherein like reference numerals refer to like elements throughout. In this regard, embodiments may be in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the embodiments.

Although the drawings depict one or more embodiments related to X-ray photography, the embodiments are not limited to such and other forms of medical imaging using electromagnetic radiation other than X-rays are contemplated.

Figure 1:
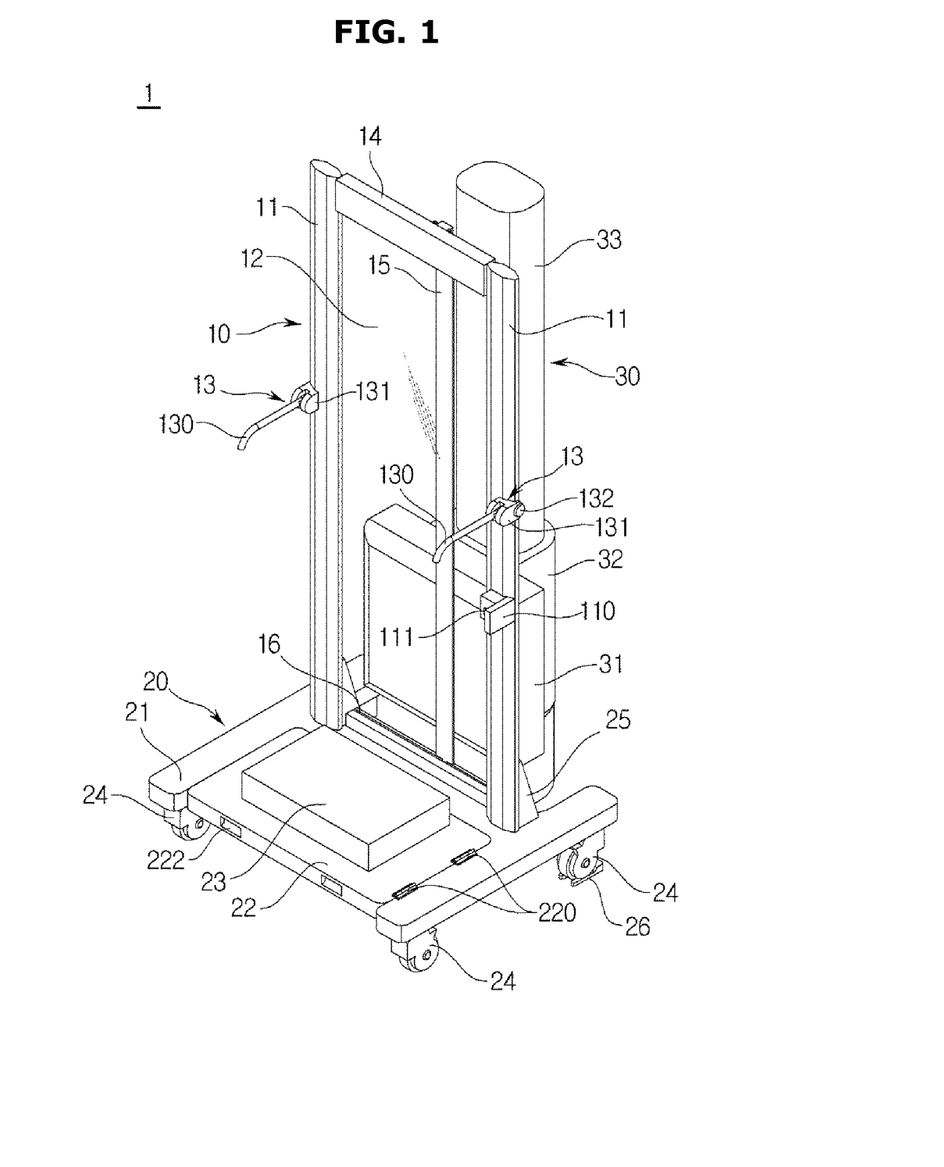
FIG. 1 is a perspective view illustrating an X-ray stitching jig in accordance with one or more embodiments.

FIG. 1 is a perspective view illustrating an X-ray stitching jig 1 in accordance with one or more embodiments.

Referring to FIG. 1, an X-ray stitching jig 1 in accordance with one or more embodiments is a subsidiary photographing apparatus for separately photographs one or more parts of a human body of a patient, and effectively stitching the separately generated images to each other. The X-ray stitching jig 1 may include a transparent plate 10, a base 20 and a detection part 30.

The transparent plate 10 may be provided in a standing type, and may be mounted on a base 20. The detection part 30 may be provided at a rear of the transparent plate 10. An object to be inspected may be positioned in front of the detection part 30. X-rays output from an X-ray generator provided in front of the object to be inspected may pass through the object to be inspected, and after passing through the transparent plate 10, may be converted into visible rays, possibly visualization of the internal tissues of the object to be inspected.

The transparent plate 10 may include side frames 11 that may be provided on an upper surface of the base 20 and a fluoroscopy window 12 that may be installed on the side frames 11 and may be formed, for example, of transparent acyl material. The side frames 11 may be provided at both sides of the fluoroscopy window 12, respectively. The side frame 11 may be provided perpendicular to the upper surface of the base 20 to fix the fluoroscopy window 12.

The side frame 11 may be provided with a handle part 13. When a patient, that is, an object to be inspected, is located in front of the fluoroscopy window 12, the patient may be subject to photographing with a hand of the patient placed on the handle part 13.

An upper frame 14 may be provided on an upper side of the fluoroscopy window 12. A lead ruler 15 may be slidably mounted on the upper frame 14. The lead ruler 15 may be provided at a rear of the fluoroscopy window 12 to recognize a position of the object photographed.

An integral type footstool 23 may be provided on the base 20. When the patient, that is, the object to be inspected, steps on the integral type footstool 23 and takes a pose for photographing, X-ray photography may be initiated. The integral type footstool 23 may protrude from the upper portion of the base 20 by a predetermined height.

The base 20 is provided at a lower surface thereof with wheels 24 that are rotatable in all directions. As the wheels 24 rotatable in all directions are provided on the lower surface of the base 20, the position of the X-ray stitching jig 1 is easily changed.

When the X-ray stitching jig 1 is placed at a desired position, the wheel 24 may be interfered by a stopper 26 to be prevented from rotating. The stopper 26 may be provided on the floor surface where the X-ray stitching jig 1 is provided, to restrict one or more of the plurality of wheels 24. Accordingly, the X-ray stitching jig 1 may be fixed not to be moved, so that the object to be inspected may be stably photographed.

A support part 25 supporting the transparent plate 10 may be provided on the base 20. The support part 25 may be provided on a portion connecting the base 20 to the transparent plate 10 to possibly prevent the transparent plate 10 from being shaken or tilted forward and backward. For example, the support part 25 may be provided on the upper surface of the base 20 to make contact with a rear surface of the transparent plate 10, to support the rear side of the transparent plate 10. Even if the transparent plate 10 is pushed in the process when the patient takes a pose for photographing, the transparent plate 10 may be stably supported by the support part 25.

The detection part 30 may be provided at a rear of the transparent plate 10. The detection part 30 may include a detector 31 to detect X-rays that may pass through the object to be inspected, a connection part 32 that may be mounted on the detector 31 and a stand 33 that may extend vertically and on which the connection part 32 may be mounted. The connection part 32 may vertically move along the stand 33. The detector 31 may detect the X-rays passing through the object to be inspected while vertically moving along an extension direction of the stand 33.

For example, the stand 33 may be provided with a rack gear in the extension direction of the stand 33, and a pinion having teeth may be provided on the connection part 32. The pinion may be connected to a motor and may rotate by the motor driven, and as the pinion rotates, the connection part 32 may move upward and downward along the stand 33 according to the rack gear. As the structure of the stand 33 is provided as above, the detector 31 may move upward and downward the stand 33.

Figure 2:
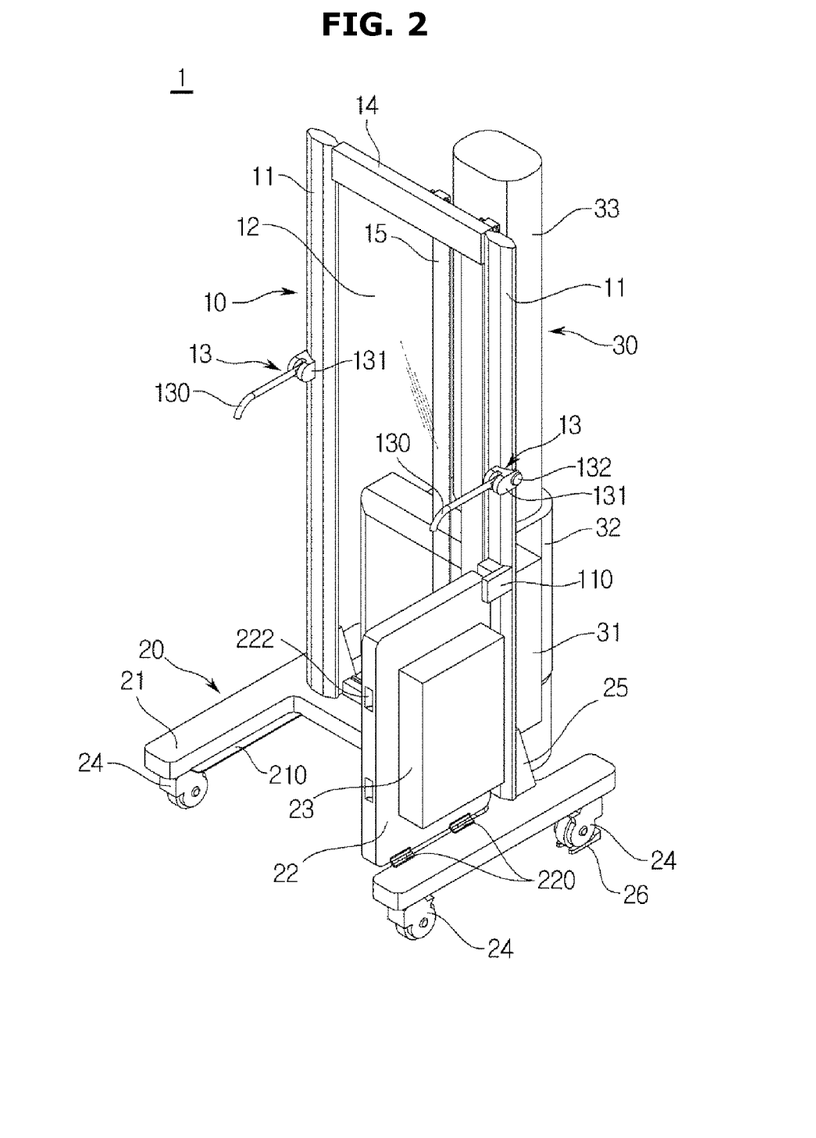
FIG. 2 is a view illustrating an integral type footstool of an X-ray stitching jig in accordance with one or more embodiments, which is folded.
Figure 3:
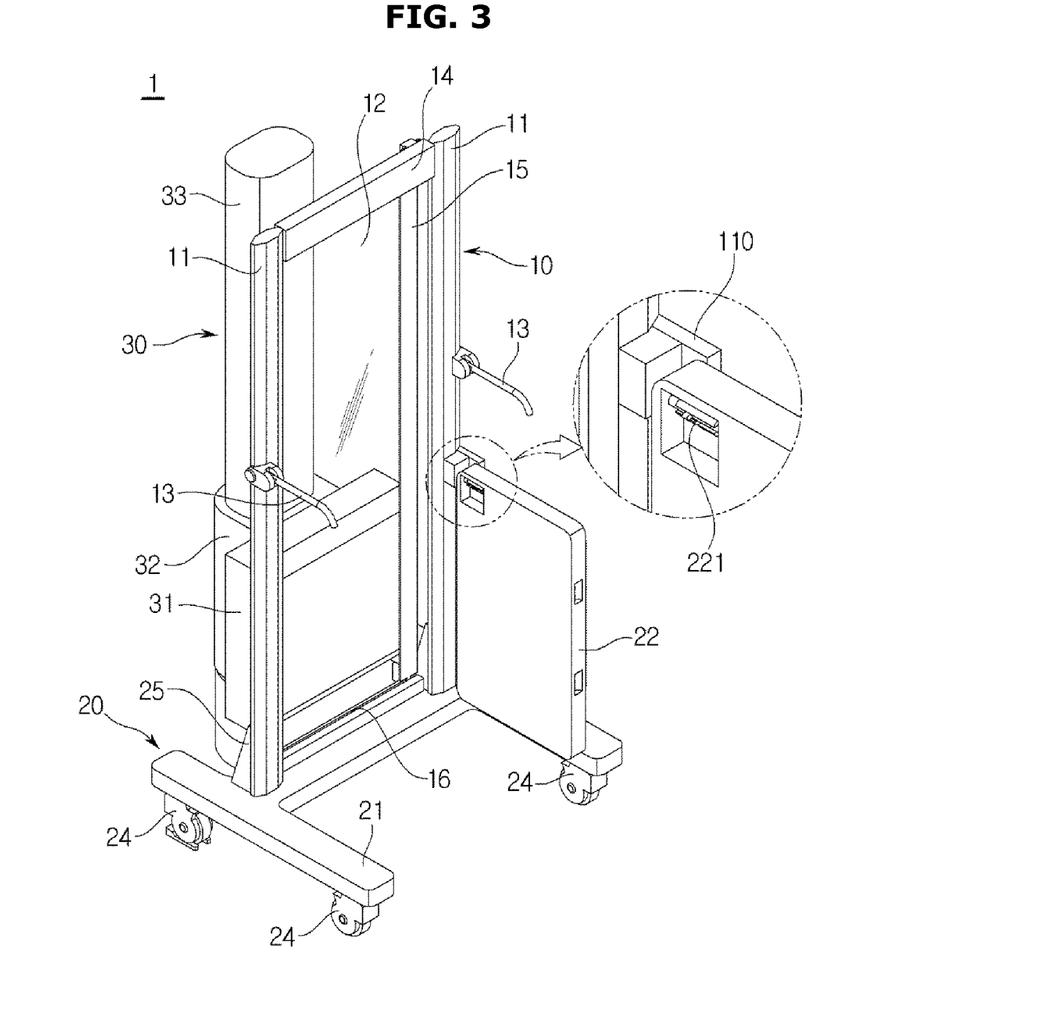
FIG. 3 is a view illustrating an integral type footstool of an X-ray stitching jig in accordance with one or more embodiments, which is folded and fixed.

FIG. 2 is a view illustrating an integral type footstool 23 of an X-ray stitching jig 1 in accordance with one or more embodiments, which is folded, and FIG. 3 is a view illustrating an integral type footstool 23 of an X-ray stitching jig 1 in accordance with one or more embodiments, which is folded to be fixed.

Referring to FIGS. 2 and 3, the integral type footstool 23 of the X-ray stitching jig 1 according to one or more embodiments may be provided in a foldable type. In particular, the base 21 may be rotatably connected to the footstool base 22 by a hinge 220, and the integral type footstool 23 may be provided on the footstool base 22.

The hinge 220 may be provided at a left side or right side of the footstool base 22. The installation direction of the hinge 220 may be changed so as to change the rotation direction of the footstool base 22 according to an environment in which the X-ray stitching jig 1 is provided. The footstool base 22 may be formed of light weighted material, and may be provided with a handle 222 that may enable the footstool base 22 to be easily folded.

The footstool base 22 may have an area equal to or larger than that of a lower surface of the integral type footstool 23. The integral type footstool 23 may have an upper surface protruding by a predetermined height from the footstool base 22.

The hinge 220 may be provided at one side of the footstool base 22 so as to possibly be rotatable by the hinge 220. The base 21 may be provided with a fixing rib 210 at a portion thereof opposed to the hinge 220. The other side of the footstool base 22 may be mounted on the fixing rib 210. If the footstool base 22 does not need to be folded, the other side of the footstool base 22 may be located to be mounted on the fixing rib 210. When the footstool base 22 is mounted on the fixing rib 210, the upper surface of the footstool base 22 may form one plane with an upper surface of the base 21.

The side frame 11 may be provided with an interference part 110 protruding forward from the side frame 11. The interference part 110 may be provided to interfere with the footstool base 22. The footstool base 22 may be rotated on the hinge 220 such that when the upper surface of the footstool base 22 contacts one surface of the interference part 110, the footstool base 22 may be interfered with the interference part 110 and thus may stop rotating. When the footstool base 22 stops rotating by being interfered with the interference part 110, the footstool base 22 may be provided in a position perpendicular to the base 21.

When the footstool base 22 is completely folded, the footstool base 22 may form an angle of about 90 degrees or above with the base 21. For example, the footstool base 22 may form an angle of about 95 degrees with the base 21. Accordingly, a patient or an X-ray photography operator may see that the footstool base 22 is completely folded at an angle of 90 degrees or above with the base 21, and thus a photographing may be performed without causing a concern that the footstool base 22 may fall.

A fixing structure may be provided to fix the footstool base 22 when the footstool base 22 is folded to be perpendicular to the base 21 by rotating through the hinge 220. The fixing structure may include an insertion part 221 provided on the footstool base 22 and an insertion hole 111 formed at the side frame 11. The insertion hole 111 may be provided adjacent to the interference part 110. The insertion part 221 may be provided to be slidably disposed at a position corresponding to the insertion hole 111 when the footstool base 22 becomes perpendicular to the base 21. The insertion part 221 provided on the footstool base 22 may be slid and inserted into the insertion hole 111 when the footstool base 22 is rotated on the hinge 220 and interfered with by the interference part 110. Accordingly, the footstool base 22 may be fixed in a folded state.

As the footstool base 22 provided with the integral type footstool 23 is fixed in a folded state, an environment for photographing may be provided to be suited to the state of the patient during photographing. For example, as for a patient having no difficulty in moving, a photographing may be performed in a state in which the footstool base 22 is mounted on the fixing rib 210 rather than folded. As for a patient having difficulty in moving and needing to be seated on a wheelchair or a chair for photographing, a photographing may be performed in a state in which the footstool base 22 is folded.

Figure 4:
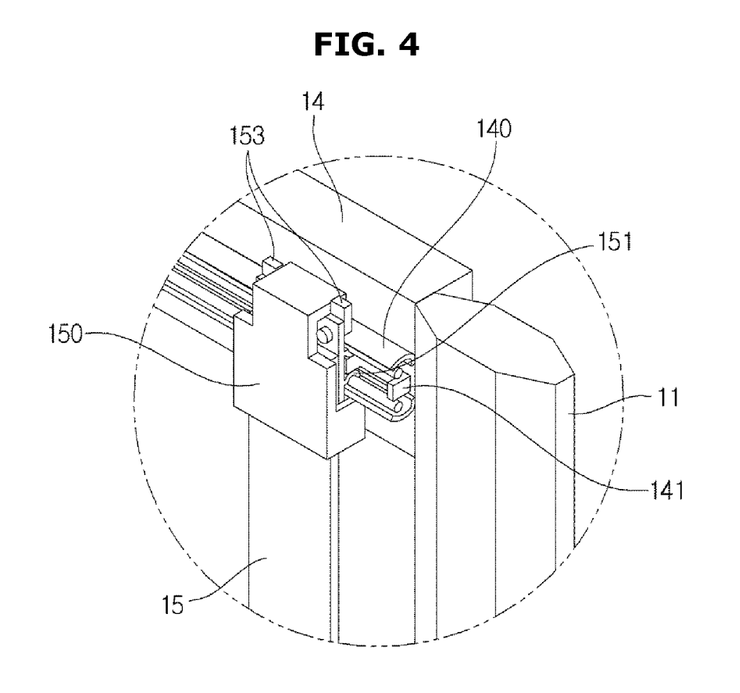
FIGS. 4 and 5 are views illustrating a sliding structure of a lead ruler provided in an X-ray stitching jig in accordance with one or more embodiments.
Figure 5:
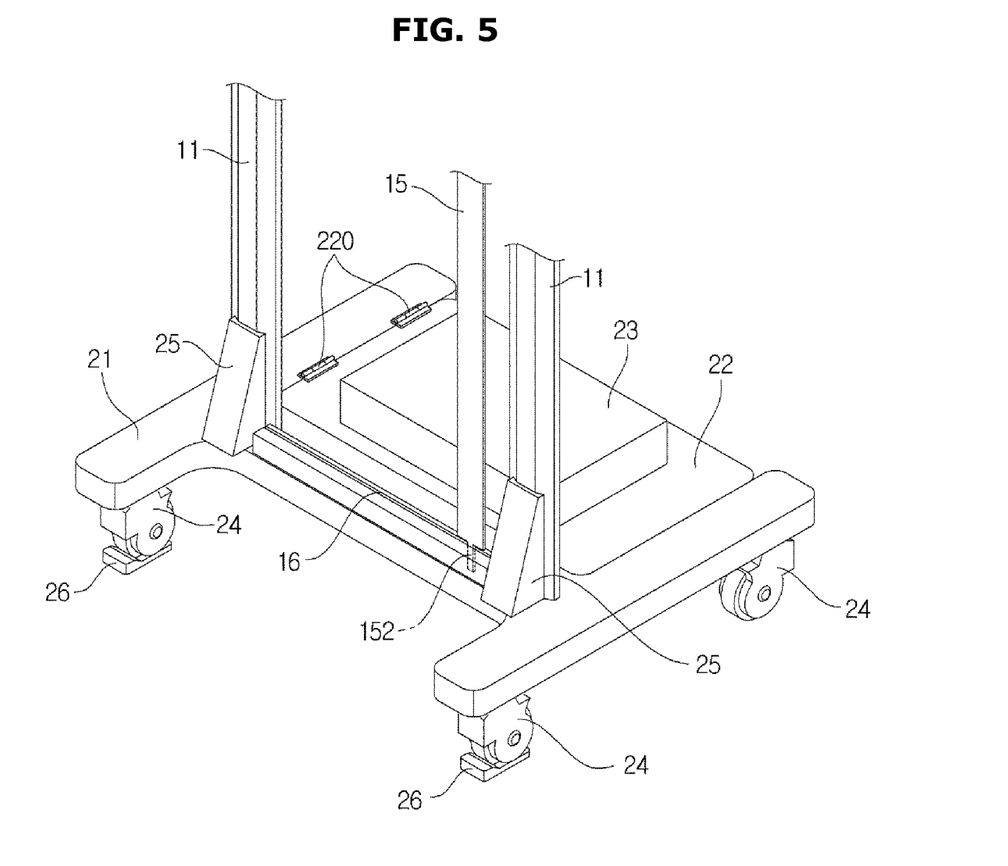

FIGS. 4 and 5 are views illustrating a sliding structure of a lead ruler 15 provided in an X-ray stitching jig 1 in accordance with one or more embodiments.

Referring to FIGS. 4 and 5, the X-ray stitching jig 1 in accordance with one or more embodiments may be provided with the lead ruler 15 that may be slidable leftward and rightward. The lead ruler 15 may be configured to identify the position in which the object to be inspected is photographed, and may be provided at a rear of the transparent plate 10.

The lead ruler 15 may be provided to be slidable on the upper frame 14. A rail 141 may be provided on a rear surface of the upper frame 14, and the lead ruler 15 may be slid leftward and rightward by the rail 141 along the upper frame 14.

A fixing bracket 150 is mounted on an upper portion of the lead ruler 15. The fixing bracket 150 may be detachably mounted on the rail 141. The fixing bracket 150 may be mounted on the rail 141 and may be slid along the rail 141. For example, the fixing bracket 150 may be provided with a sliding part 151 that is mounted on the rail 141 while surrounding a portion of the rail 141, and the sliding part 151 may be slid along the rail 141. Accordingly, the lead ruler 15 may be slid leftward and rightward along the rail 141.

The upper frame 14 may be further provided with a guide rail 140 at a rear surface of the upper frame 14. The guide rail 140 may guide the fixing bracket 150 to be stably slid along the rail 141. For example, one side of the fixing bracket 150 may be mounted on the upper surface of the guide rail 140 and slid. The fixing bracket 150 may be provided with a mounting part 153. The mounting parts 153 may be provided at both sides of the fixing bracket 150, respectively. The mounting part 153 may be mounted on the upper surface of the guide rail 140 and may be slid along the guide rail 140.

A protrusion part 152 may be formed at a lower portion of the lead ruler 15. A rail groove 16 may be formed on the base 21 located at a rear of the transparent plate 10. The protrusion part 152 provided at the lower portion of the lead ruler 15 may be inserted into the rail groove 16 and slid. As the fixing bracket 150 provided on the upper portion of the lead ruler 15 may be slid along the rail 141, the protrusion part 152 provided at the lower portion of the lead ruler 15 may be guided along the rail groove 16, and may be slid along the rail groove 16.

As the lead ruler 15 may be provided to be slid leftward and rightward along the rail 141, the position of the lead ruler 15 may be changed depending on the environment for imaging. In addition, the lead ruler 15 may be detachably provided to be separated from the transparent plate 10 when the lead ruler 15 is not needed.

Figure 6:
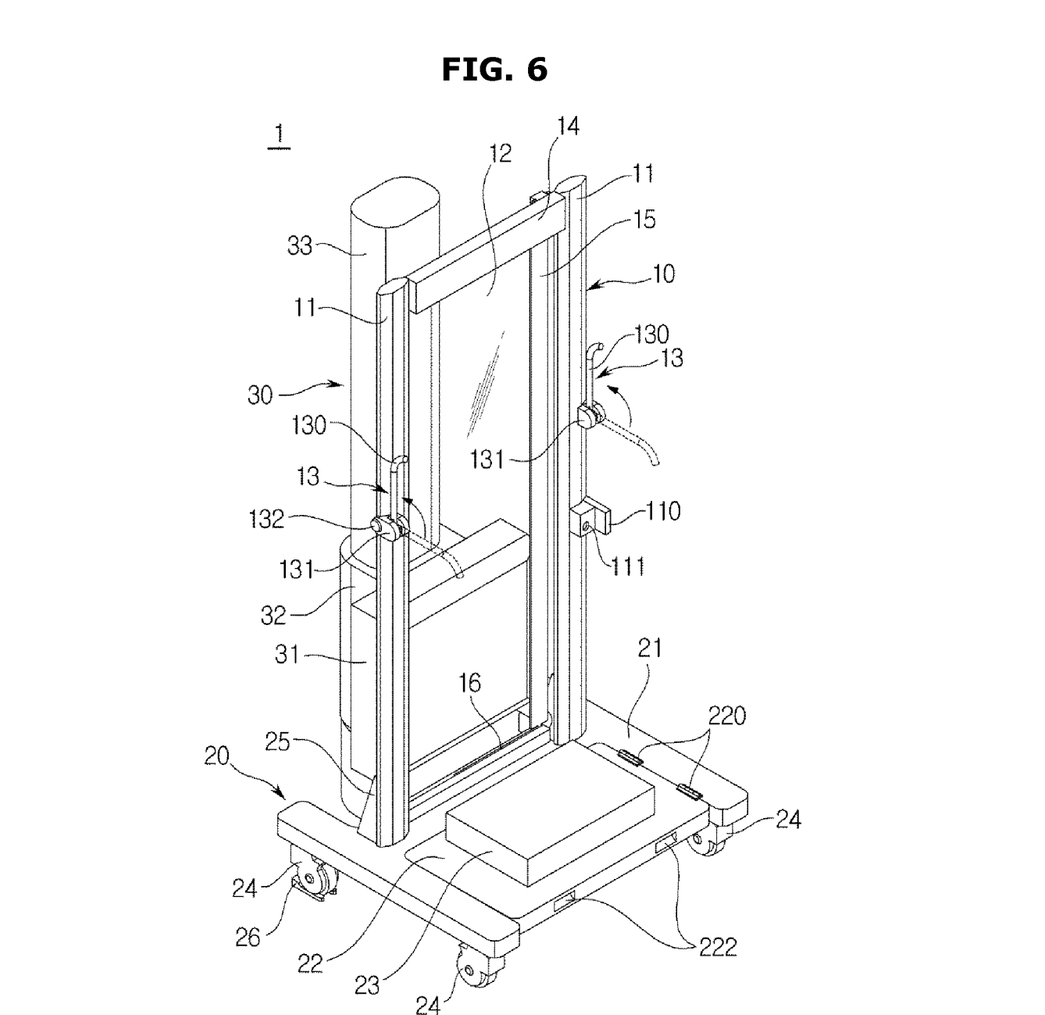
FIG. 6 is a view illustrating a handle part provided in an X-ray stitching jig in accordance with one or more embodiments, which is folded.

FIG. 6 is a view illustrating a handle part 13 provided in an X-ray stitching jig 1 in accordance with one or more embodiments, which is folded.

Referring to FIG. 6, the handle part 13 in accordance with one or more embodiments may be foldably provided on the X-ray stitching jig 1. The handle part 13 may be provided on the side frame 11.

The handle part 13 may include a handle 130, a mounting part 131 and a rotating shaft 132. The handle 130 may be provided so as to be rotatable by the rotating shaft 132. The mounting part 131 may be provided on the side frame 11 in a protruding manner. The rotating shaft 132 may be provided to pass through the mounting part 131 and the handle 130. The mounting part 131 may be provided to protrude forward from the side frame 11. The handle 130 may be projected forward from the transparent plate 10, or may be folded such that one end portion of the handle 130 is adjacent to the side frame 11 as the handle 130 rotates on the rotating shaft 132.

As the handle part 13 is foldably provided, a patient, that is, an object to be inspected, may be positioned in front of the transparent plate 10 in a state that the handle part 13 is folded in consideration of the state of the patient. Accordingly, an environment for safely and effectively photographing a patient having difficulty in movement may be provided.

As is apparent from the above, the X-ray stitching jig 1 according to one or more embodiments is provided with a handle part and an integral type foldable footstool 23 so as to be foldable, so that a patient who is difficult in moving can have an effective X-ray imaging without being interfered by the handle part 13 and the integral type footstool 23. In addition, the X-ray stitching jig 1 is provided with the integral type footstool 23 a lead ruler 15 at a rear surface thereof so as to be slidable leftward and rightward and also detachable, which enables the lead ruler 15 to be detached and changed in position in consideration of convenience at the time of photographing, and the X-ray stitching jig 1 is also provided with wheels 24 at a lower end thereof that are rotatable in all directions, which may enable easy movement of the X-ray stitching jig 1.

While aspects have been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. An X-ray apparatus comprising:
    an X-ray generator generating X-rays;
    a detection part detecting X-rays passed through an object to be inspected; and
    an X-ray stitching jig positioned on one side of the detection part,
    the X-ray stitching jig comprising:
        a base;
        a transparent window provided above the base; and
        a footstool base comprising a footstool and a hinge, and rotatably connected to the base by the hinge.

2. The X-ray apparatus of claim 1, wherein the base comprises a fixing rib and the footstool base is seated on the fixing rib to be fixed.

3. The X-ray apparatus of claim 2, wherein when the footstool base is seated on the fixing rib, an upper surface of the footstool base forms one plane with an upper surface of the base.

4. The X-ray apparatus of claim 1, further comprising side frames provided at both sides of the transparent window to support the transparent window.

5. The X-ray apparatus of claim 4, wherein one side frame of the side frames comprises an interference part that protrudes forward from the one side frame.

6. The X-ray apparatus of claim 5, wherein the footstool base is configured to rotate on the hinge and interfered with the interference part.

7. The X-ray apparatus of claim 4, wherein the footstool base comprises an insertion part, and one side frame of the side frames comprises an insertion hole into which the insertion part is inserted.

8. The X-ray apparatus of claim 7, wherein as the footstool base rotates on the hinge, the insertion part is slidably inserted into the insertion hole, so that the footstool base is folded to be perpendicular to the base.

9. The X-ray apparatus of claim 4, wherein one side frame of the side frames comprises a handle that is foldable.

10. The X-ray apparatus of claim 9, wherein the one side frame of the side frames further comprises a rotating shaft that passes through the handle and a mounting part protruding from the one side frame, and wherein the handle is configured to be rotatable on the rotating shaft.

11. The X-ray apparatus of claim 1, wherein the X-ray stitching Jig further comprises a lead ruler slidably provided at a rear of the transparent window.

12. The X-ray apparatus of claim 11, wherein the X-ray stitching jig further comprises an upper frame provided at an upper side of the transparent window, and a guide rail provided at a lower surface of the upper frame, so that the lead ruler is slidable leftward and rightward along the guide rail.

13. The X-ray apparatus of claim 12, wherein the X-ray stitching jig further comprises a fixing bracket mounted on an upper portion of the lead ruler, and mounted on the guide rail so as to be slid along the guide rail.

14. The X-ray apparatus of claim 13, wherein one side of the fixing bracket is mounted on an upper surface of the guide rail so as to be slid along the guide rail.

15. The X-ray apparatus of claim 13, wherein the X-ray stitching jig further comprises the fixing bracket is detachably mounted on the guide rail.

16. The X-ray apparatus of claim 11, wherein the X-ray stitching jig further comprises a rail groove formed on the base, and the lead ruler comprises a protrusion part on a lower portion of the lead ruler and the protrusion part is guided by the rail groove.

17. The X-ray apparatus of claim 1, wherein the X-ray stitching Jig further comprises a support part provided at a portion connecting the base to the transparent window to support the transparent window.

18. The X-ray apparatus of claim 1, wherein the base comprises a wheel at a lower portion thereof, and wherein the wheel is rotatable in all directions.

19. The X-ray apparatus of claim 18, wherein the X-ray stitching jig further comprises a stopper positioned on a bottom surface to restrict the wheel from rotating.

20. The X-ray apparatus of claim 1, wherein the detection part is provided on a rear side of the transparent window and configured to move upward and downward.

21. The X-ray apparatus of claim 1, wherein the footstool base allows a position of the hinge to be changed such that rotation direction of the footstool base is changed depending on an environment in which the X-ray stitching jig is used.

22. A medical imaging apparatus comprising:
  a generator generating electromagnetic radiation;
  a detection part detecting electromagnetic radiation passing through an object to be inspected and configured to move upward and downward; and
  a medical imaging jig positioned on one side of the detection part,
  the medical imaging jig comprising:
    a base;
    a footstool base comprising a footstool and a hinge, and rotatably connected to the base by the hinge; and
    a lead ruler slidably provided above the base and in front of the detection part.

23. The medical imaging apparatus of claim 22, wherein the medical imaging jig further comprises:
  side frames extending upward from the base;
  an upper frame provided at an upper end of each of the side frames and connecting the side frames; and
  a guide rail provided at a lower surface of the upper frame, so that the lead ruler is slidable leftward and rightward along the guide rail.

24. The medical imaging apparatus of claim 23, wherein one side frame of the side frames comprises a handle that is foldable.

25. The medical imaging apparatus of claim 24, wherein the one side frame of the side frames further comprises a rotating shaft that passes through the handle and a mounting part protruding from the one side frame, and wherein the handle is configured to be rotatable on the rotating shaft.

26. The medical imaging apparatus of claim 22, wherein the medical imaging jig further comprises a rail groove formed on the base, and the lead ruler comprises a protrusion part on a lower portion of the lead ruler and the protrusion part is guided by the rail groove.

27. The medical imaging apparatus of claim 22, wherein the base comprises a fixing rib and the footstool base is seated on the fixing rib to be fixed, and when the footstool base is seated on the fixing rib, an upper surface of the footstool base forms one plane with an upper surface of the base.

* * * * *